United States Patent
Lee et al.

(10) Patent No.: US 10,164,725 B2
(45) Date of Patent: Dec. 25, 2018

(54) METHOD OF MEASURING TIME DIFFERENCE BETWEEN DETECTION TIMES, AND DEVICE FOR PERFORMING THE METHOD

(71) Applicant: SAMSUNG ELECTRONICS CO., LTD., Suwon-si (KR)

(72) Inventors: Jaechun Lee, Seoul (KR); Ui Kun Kwon, Hwaseong-si (KR); Seungkeun Yoon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 209 days.

(21) Appl. No.: 15/072,867

(22) Filed: Mar. 17, 2016

(65) Prior Publication Data

US 2017/0078036 A1    Mar. 16, 2017

(30) Foreign Application Priority Data

Sep. 15, 2015    (KR) .................. 10-2015-0130168

(51) Int. Cl.
*H04J 3/06*    (2006.01)
*A61B 5/024*    (2006.01)

(52) U.S. Cl.
CPC .............. *H04J 3/06* (2013.01); *A61B 5/024* (2013.01)

(58) Field of Classification Search
CPC .............. A61B 5/02416; A61B 5/1118; A61B 5/02055; A61B 5/02438; A61B 5/0245; A61B 5/0402; A61B 5/0816; A61B 5/4866; A61B 5/6814; A61B 2562/0247; A61B 2560/0468; A61B 2562/046; A61B 5/02007; A61B 5/022; A61B 5/0404; A61B 5/103; A61B 5/1102; A61B 5/113; A61B 5/14557; A61B 5/6887; A61B 3/1241;
(Continued)

(56) References Cited

U.S. PATENT DOCUMENTS

| | | | |
|---|---|---|---|
| 7,310,549 B1 | 12/2007 | Angelini et al. | |
| 7,333,725 B1 * | 2/2008 | Frazier | G03B 31/04 348/207.99 |
| 8,718,938 B2 | 5/2014 | Wolf et al. | |

(Continued)

FOREIGN PATENT DOCUMENTS

| | | |
|---|---|---|
| JP | 2014-217707 A | 11/2014 |
| KR | 10-1337387 B1 | 12/2013 |

OTHER PUBLICATIONS

McCombie et al., "Adaptive blood pressure estimation from wearable PPG sensors using peripheral artery pulse wave velocity measurements and multi-channel blind identification of local arterial dynamics," *Engineering in Medicine and Biology Society*, 2006. EMBS '06. 28th Annual International Conference of the IEEE, New York, NY, 2006, pp. 3521-3524.

*Primary Examiner* — Ajibola A Akinyemi
(74) *Attorney, Agent, or Firm* — NSIP Law

(57) ABSTRACT

A method of measuring a time difference between detection times includes receiving, from a first sensor, first information associated with a first detection time at which a first biosignal is detected, receiving, from a second sensor, second information associated with a second detection time at which a second biosignal is detected, and measuring a time difference between the first and the second detection times based on the first information and the second information.

20 Claims, 18 Drawing Sheets

(58) Field of Classification Search
CPC ... A61B 5/0002; A61B 5/0022; A61B 5/0205; A61B 5/02125
USPC ........................................................ 455/41.1
See application file for complete search history.

(56) References Cited

U.S. PATENT DOCUMENTS

| | | |
|---|---|---|
| 8,838,209 B2 | 9/2014 | Mestha et al. |
| 2005/0137827 A1* | 6/2005 | Takamiya ............ G01B 11/002 702/150 |
| 2007/0164752 A1 | 7/2007 | Kato |
| 2008/0103702 A1* | 5/2008 | Ando ..................... A61B 5/103 702/41 |
| 2008/0200772 A1 | 8/2008 | Shimizu |
| 2012/0007740 A1* | 1/2012 | Kangas ............. H04M 1/72569 340/573.1 |
| 2012/0302899 A1* | 11/2012 | Yook .................... A61B 5/0507 600/484 |
| 2013/0119773 A1* | 5/2013 | Davis ..................... H02J 5/005 307/104 |
| 2014/0276123 A1 | 9/2014 | Yang |

\* cited by examiner

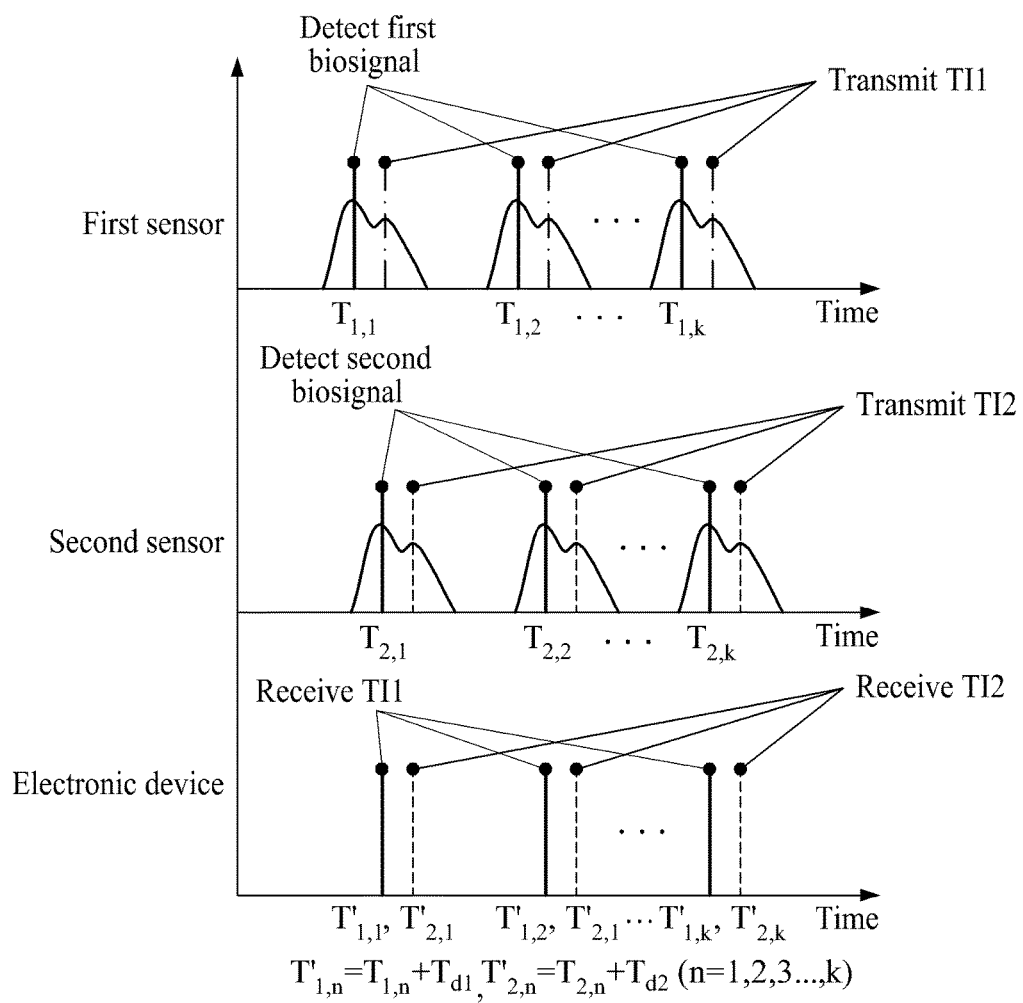

METHOD OF MEASURING TIME DIFFERENCE BETWEEN DETECTION TIMES, AND DEVICE FOR PERFORMING THE METHOD

CROSS-REFERENCE TO RELATED APPLICATION(S)

This application claims the benefit under 35 USC 119(a) of Korean Patent Application No. 10-2015-0130168 filed on Sep. 15, 2015, in the Korean Intellectual Property Office, the entire disclosure of which is incorporated herein by reference for all purposes.

BACKGROUND

1. Field

The following description relates to a method of measuring a time difference between detection times and a device for performing the method.

2. Description of Related Art

To obtain a pulse transit time (PTT), biosignal sensing devices located in different portions of a body are connected by a wire, and photoplethysmogram (PPG) signal waveforms are continuously collected from each biosignal sensing device. The PTT is calculated by comparing the collected signal waveforms.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of measuring a time difference between detection times includes receiving, from a first sensor, first information associated with a first detection time at which a first biosignal is detected; receiving, from a second sensor, second information associated with a second detection time at which a second biosignal is detected; and measuring a time difference between the first detection time and the second detection time based on the first information and the second information.

The first information and the second information may be time information synchronized with absolute time information.

The first information and the second information may be time information synchronized with relative time information.

The method may further include receiving a beacon signal; and the measuring may include calculating the time difference between the first detection time and the second detection time based on the first information, the second information, and a receipt time at which the beacon signal is received.

The first information and the second information may be time information synchronized based on the receipt time at which the beacon signal is received.

The method may further include receiving a first beacon signal transmitted from the first sensor; and receiving a second beacon signal transmitted from the second sensor; and the measuring may include calculating the time difference between the first detection time and the second detection time based on the first information, the second information, a receipt time at which the first beacon signal is received, and a receipt time at which the second beacon signal is received.

The first information may be time information synchronized based on the first beacon signal; and the second information may be time information synchronized based on the second beacon signal.

The measuring may include measuring a first receipt time at which the first information is received; measuring a second receipt time at which the second information is received; and calculating the time difference between the first detection time and the second detection time based on the first receipt time and the second receipt time.

In another general aspect, an electronic device includes an interface configured to receive, from a first sensor, first information associated with a first detection time at which a first biosignal is received, and receive, from a second sensor, second information associated with a second detection time at which a second biosignal is received; and a controller configured to measure a time difference between the first detection time and the second detection time based on the first information and the second information.

The first information and the second information may be time information synchronized with absolute time information.

The first information and the second information may be time information synchronized with relative time information.

The interface may be further configured to receive, from a beacon device, a beacon signal; and the controller may be further configured to calculate the time difference between the first detection time and the second detection time based on the first information, the second information, and a receipt time at which the beacon signal is received.

The first information and the second information may be time information synchronized based on the receipt time at which the beacon signal is received.

The interface may be further configured to receive a first beacon signal transmitted from the first sensor, and receive a second beacon signal transmitted from the second sensor; and the controller may be further configured to calculate the time difference between the first detection time and the second detection time based on the first information, the second information, a receipt time at which the first beacon signal is received, and a receipt time at which the second beacon signal is received.

The first information may be time information synchronized based on the first beacon signal; and the second information may be time information synchronized based on the second beacon signal.

The controller may be further configured to measure a first receipt time at which the first information is received and a second receipt time at which the second information is received, and calculate the time difference between the first detection time and the second detection time based on the first receipt time and the second receipt time.

The controller may be further configured to receive either one or both of the first information and the second information using coils coupled by a magnetic field.

The controller may be further configured to receive the either one or both of the first information and the second information by mutual magnetic induction between the coils occurring due to charging and discharging of a resonator.

The controller may be further configured to receive the either one or both of the first information and the second information by mutual magnetic induction between the coils occurring due to an oscillator switching between ON and OFF states.

The controller may be further configured to transmit power to either one or both of the first sensor and the second sensor using the coils coupled by the magnetic field.

Other features and aspects will be apparent from the following detailed description, the drawings, and the claims.

BRIEF DESCRIPTION OF THE DRAWINGS

FIGS. 9A and 9B are diagrams illustrating another example of a method of measuring a time difference between detection times.

Throughout the drawings and the detailed description, the same drawing reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 1:
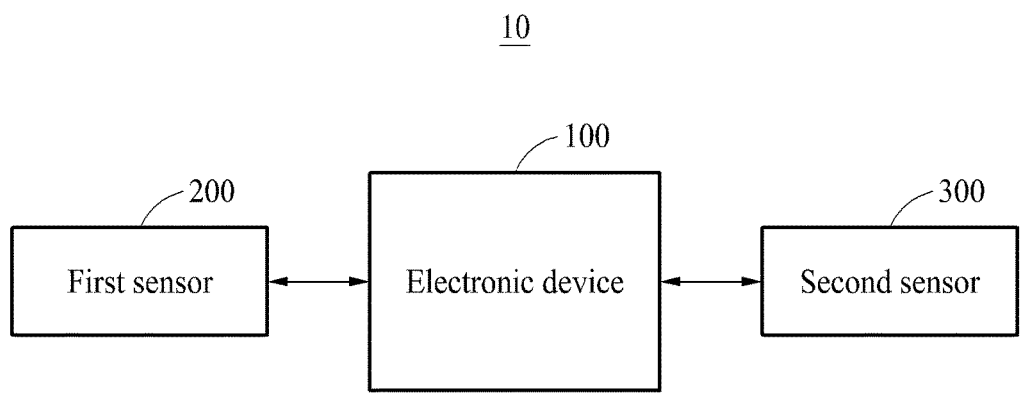
FIG. 1 is a diagram illustrating an example of an electronic system.

FIG. 1 is a diagram illustrating an example of an electronic system 10.

Referring to FIG. 1, the electronic system 10 includes an electronic device 100, a first sensor 200, and a second sensor 300.

The first sensor 200 and the second sensor 300 are worn on different portions of a body of a user to sensor a biosignal. A biosignal is any type of signal that may be measured, monitored, detected, or sensed from a biological being continuously, intermittently, or one time, and is unique for each biological being. For example, the biosignal may be an electrocardiogram (ECG) signal, a photoplethysmogram (PPG) signal, an electromyogram (EMG) signal, a voice, or an impedance generated from the body.

The first sensor 200 detects or senses a first biosignal from the user wearing the first sensor 200. The first sensor 200 generates first information associated with a first detection time at which the first biosignal is detected. The first sensor 200 transmits the first information to the electronic device 100.

The second sensor 300 detects or senses a second biosignal from the user wearing the second sensor 300. The second sensor 300 generates second information associated with a second detection time at which the second biosignal is detected. The second sensor 300 transmits the second information to the electronic device 100.

The first sensor 200 and the second sensor 300 wirelessly communicate with the electronic device 100.

The electronic device 100 receives the first information transmitted from the first sensor 200, and the second information transmitted from the second sensor 300. The electronic device 100 measures a time difference between the first detection time of the first biosignal detected by the first sensor 200 and the second detection time of the second biosignal detected by the second sensor 300 based on the first information and the second information. The time difference may be, for example, a pulse transit time (PPT).

The sensors 200 and 300 may transmit information associated with a detection time instead of a real-time biosignal waveform, and thus a transmission bandwidth and a transmission power may be reduced. In addition, a processing speed of the electronic device 100 may increase and an amount of power consumption may be reduced.

Figure 2:
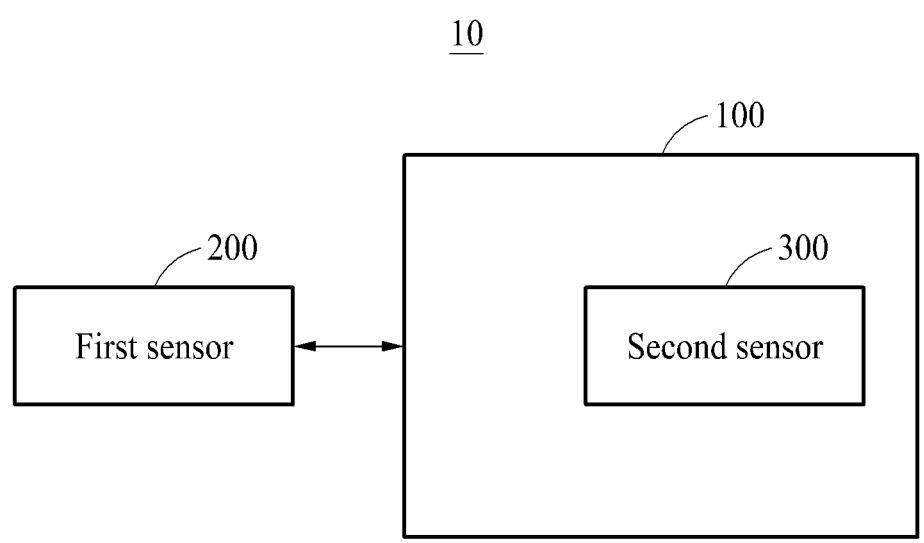
FIG. 2 is a diagram illustrating another example of an electronic system.
Figure 3:
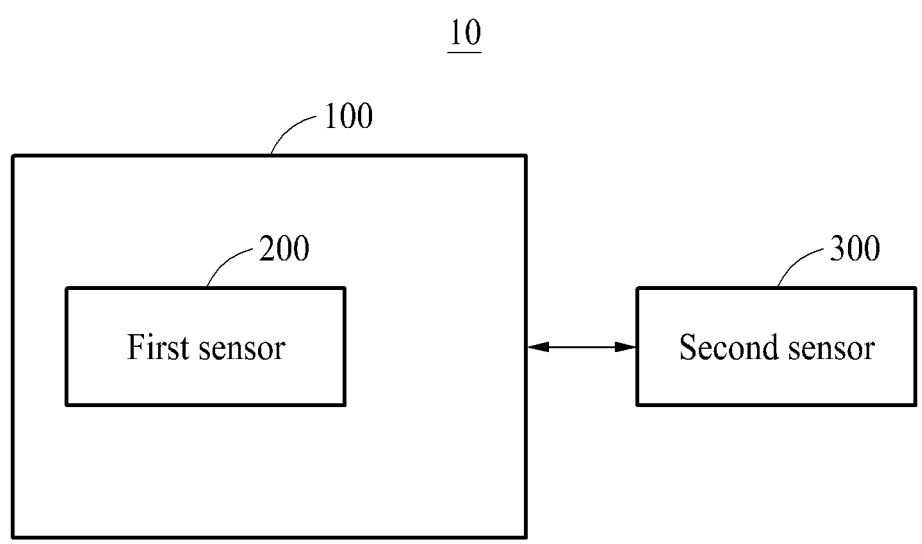
FIG. 3 is a diagram illustrating another example of an electronic system.
Figure 4:
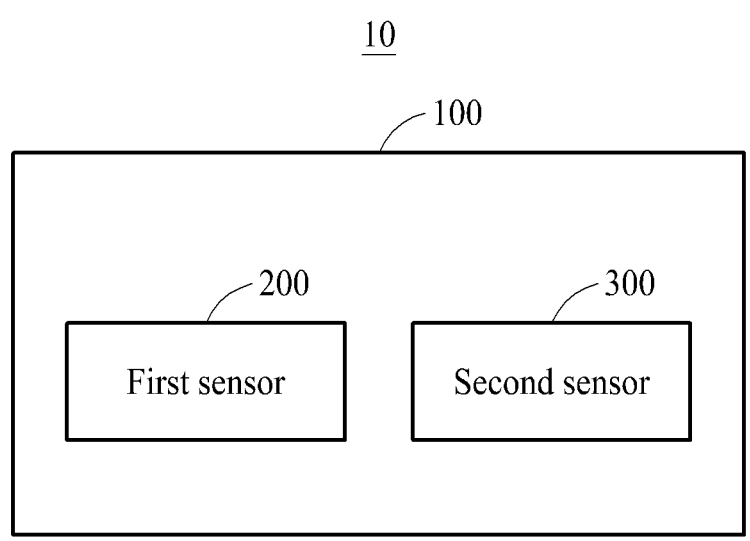
FIG. 4 is a diagram illustrating another example of an electronic system.

FIGS. 2 through 4 are diagrams illustrating other examples of the electronic system 10. As illustrated in FIG. 2, the second sensor 300 is included in the electronic device 100. As illustrated in FIG. 3, the first sensor 200 is included in the electronic device 100. As illustrated in FIG. 4, the sensors 200 and 300 are included in the electronic device 100. That is, in the examples in FIGS. 2 through 4, either one or both of the first sensor 200 and the second sensor 300 is included in the electronic device 100. Thus, either one or both of the first sensor 200 and the second sensor 300 may be connected to the electronic device 100 by a wire.

Figure 5:
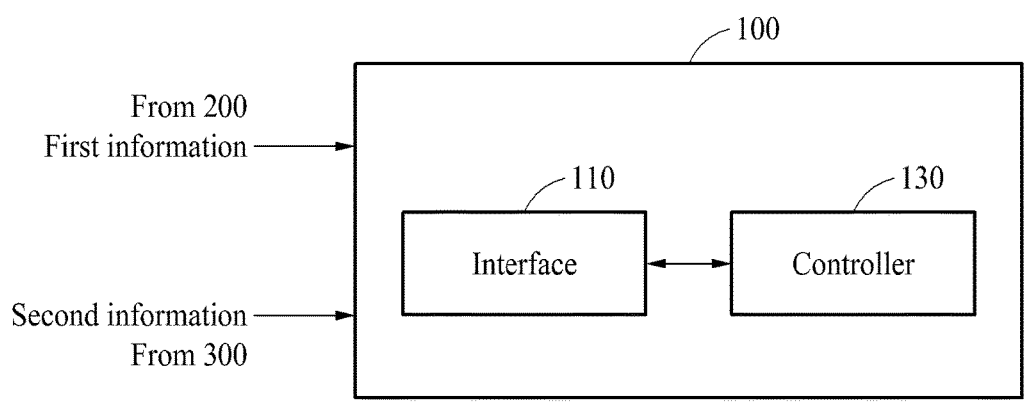
FIG. 5 is a diagram illustrating an example of an electronic device.

FIG. 5 is a diagram illustrating an example of the electronic device 100.

Referring to FIGS. 1 through 5, the electronic device 100 includes an interface 110 and a controller 130.

The electronic device 100 may be provided in the form of a personal computer (PC), a data server, or a portable device.

The portable device may be, for example, a laptop computer, a mobile phone, a smartphone, a tablet PC, a mobile Internet device (MID), a personal digital assistant (PDA), an enterprise digital assistant (EDA), a digital still camera, a digital video camera, a portable multimedia player (PMP), a personal or portable navigation device (PND), a handheld game console, an e-book, or a smart device.

The smart device may be, for example, a smart watch or a smart band.

The electronic device 100 may be a wearable device to be worn on a user or suitable for being worn.

The interface 110 receives first information transmitted from the first sensor 200, and second information transmitted from the second sensor 300.

The controller 130 controls an overall operation of the electronic device 100. The controller 130 receives the first information and the second information through the interface 110.

The controller 130 measures a time difference between a first detection time at which a first biosignal is detected by the first sensor 200 and a second detection time at which a second biosignal is detected by the second sensor 300 based on the first information and the second information.

Although FIG. 5 illustrates the electronic device 100 in which the interface 110 and the controller 130 as being separate from each other, the interface 110 may be included in the controller 130 in another example.

Hereinafter, a method of measuring a time difference between detection times will be described in detail with reference to FIGS. 6A through 9B.

Figure 6A:
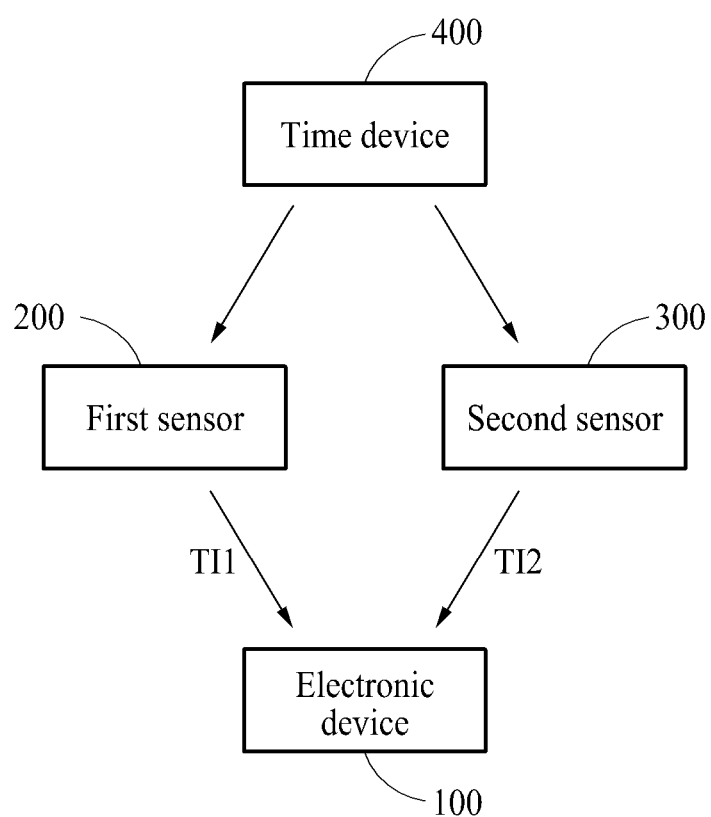
FIGS. 6A and 6B are diagrams illustrating an example of a method of measuring a time difference between detection times.
Figure 6B:
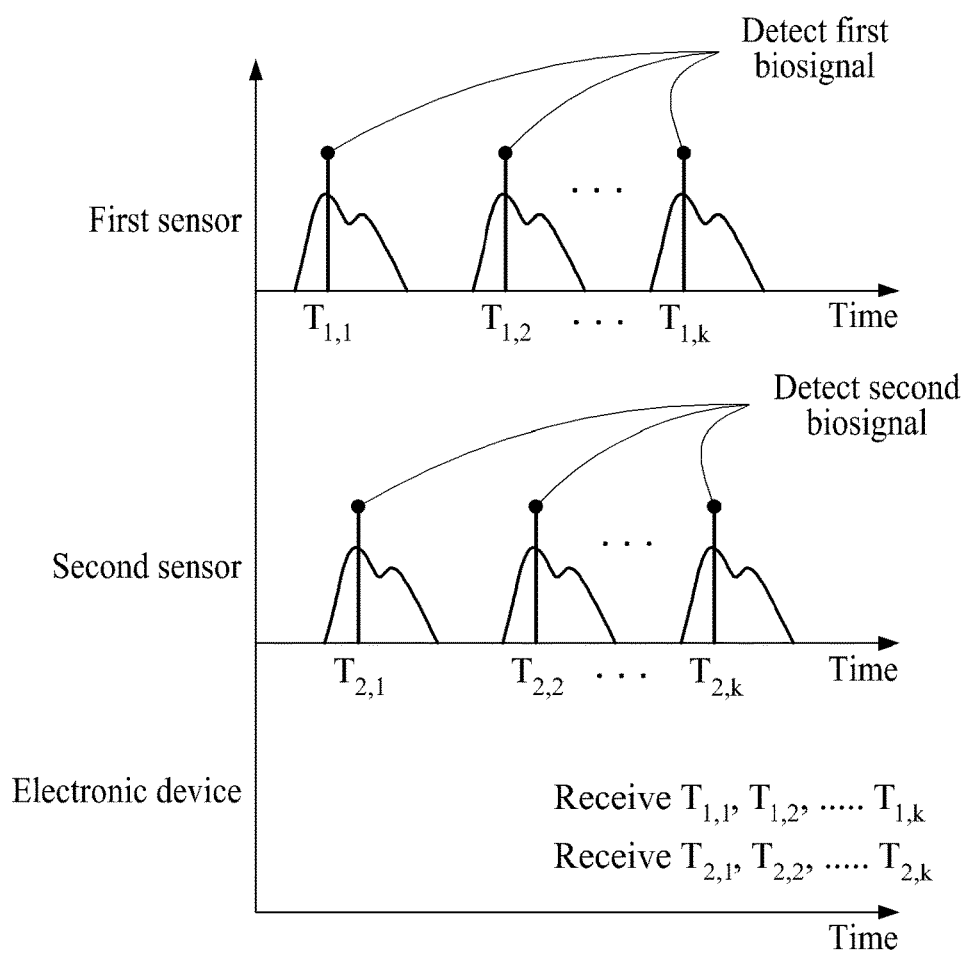

FIGS. 6A and 6B are diagrams illustrating an example of a method of measuring a time difference between detection times.

Referring to FIGS. 6A and 6B, a time device 400 transmits absolute time information to the first sensor 200 and the second sensor 300. The first sensor 200 and the second sensor 300 synchronize an internal time based on the absolute time information transmitted from the time device 400. That is, an internal clock of the first sensor 200 and an internal clock of the second sensor 300 are synchronized to correspond to each other. The time device 400 is a device that provides absolute time information, for example, a global positioning system (GPS) satellite server and an atomic clock device.

A first detection time, for example, $T_{1,1}$, $T_{1,2}$, and $T_{1,k}$, at which a first biosignal is detected by the first sensor 200 is synchronized with the absolute time information. The first sensor 200 generates first information, for example, TI1, associated with the first detection time $T_{1,1}$ through $T_{1,k}$ at which the first biosignal is detected. The first sensor 200 generates the first information TI1 synchronized with the absolute time information.

A second detection time, for example, $T_{2,1}$, $T_{2,2}$, and $T_{2,k}$, at which a second biosignal is detected by the second sensor 300 is synchronized with the absolute time information. The second sensor 300 generates second information, for example, TI2, associated with the second detection time $T_{2,1}$ through $T_{2,k}$ at which the second biosignal is detected. The second sensor 300 generates the second information TI2 synchronized with the absolute time information.

The first information TI1 transmitted from the first sensor 200 and the second information TI2 transmitted from the second sensor 300 are time information synchronized with the absolute time information. Thus, the first information TI1 and the second information TI2 are absolute time information.

The time device 400 may also transmit the absolute time information to the electronic device 100. In contrast to the first sensor 200 and the second sensor 300, the electronic device 100 may not need such time synchronization.

The controller 130 calculates a time difference, for example, $\Delta T_n$, between the first detection time $T_{1,1}$ through $T_{1,k}$ at which the first biosignal is detected by the first sensor 200 and the second detection time $T_{2,1}$ through $T_{2,k}$ at which the second biosignal is detected by the second sensor 300 based on the first information TI1 and the second information TI2.

For example, the controller 130 calculates the time difference $\Delta T_n$ between the first detection time $T_{1,1}$ through $T_{1,k}$ and the second detection time $T_{2,1}$ through $T_{2,k}$ according to Equation 1 below.

$$\Delta T_n = T_{2,n} - T_{1,n} (n=1,2,3,\ldots k) \quad (1)$$

Figure 7A:
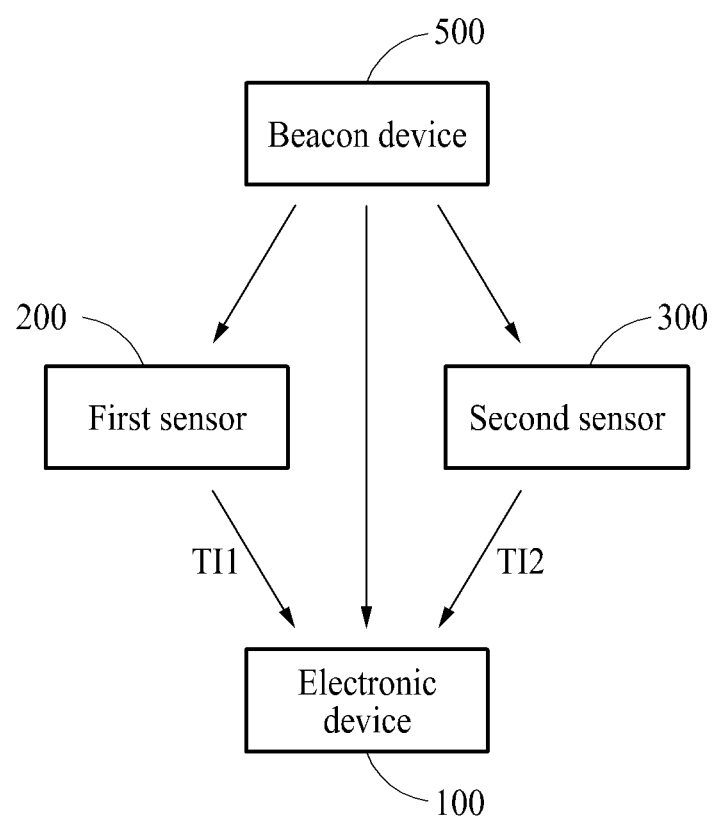
FIGS. 7A and 7B are diagrams illustrating another example of a method of measuring a time difference between detection times.
Figure 7B:
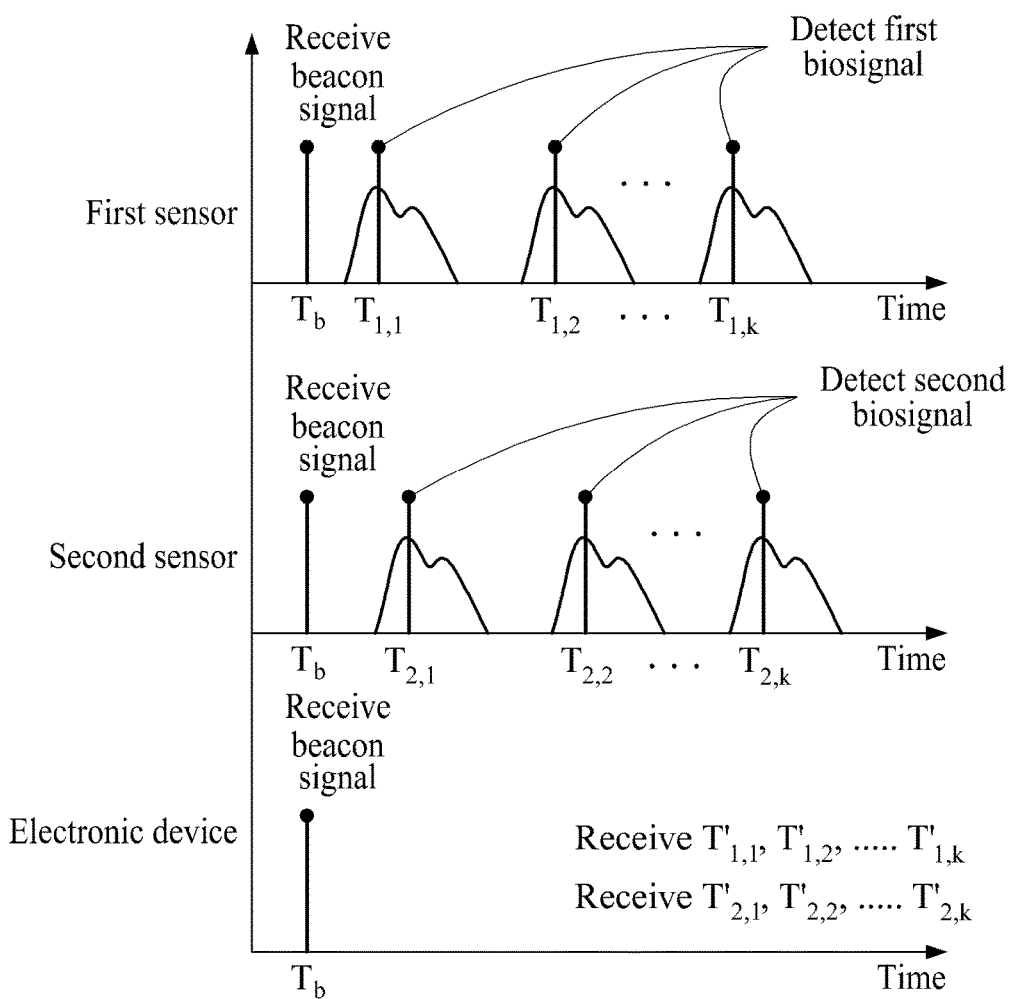

FIGS. 7A and 7B are diagrams illustrating another example of a method of measuring a time difference between detection times.

Referring to FIGS. 7A and 7B, a beacon device 500 generates relative time information, for example, a beacon signal, and transmits the generated beacon signal to the first sensor 200, the second sensor 300, and the electronic device 100. The first sensor 200 and the second sensor 300 are synchronized based on the beacon signal. For example, the first sensor 200 and the second sensor 300 are synchronized based on a receipt time $T_b$ at which the beacon signal is received.

A first detection time, for example, $T_{1,1}$, $T_{1,2}$, and $T_{1,k}$, at which a first biosignal is detected by the first sensor 200 is synchronized based on the receipt time $T_b$ at which the beacon signal is received. The first sensor 200 generates first information TI1 associated with the first detection time $T_{1,1}$ through $T_{1,k}$ at which the first biosignal is detected. The first sensor 200 generates the first information TI1 synchronized based on the receipt time $T_b$ at which the beacon signal is received.

A second detection time, for example, $T_{2,1}$, $T_{2,2}$, and $T_{2,k}$, at which a second biosignal is detected by the second sensor 300 is synchronized based on the receipt time $T_b$ at which the beacon signal is received. The second sensor 300 generates second information TI2 associated with the second detection time $T_{2,1}$ through $T_{2,k}$ at which the second biosignal is detected. The second sensor 300 generates the second information TI2 synchronized based on the receipt time $T_b$ at which the beacon signal is received.

The first information TI1 includes relative time information expressed by Equation 2 below.

$$T'_{1,n} = T_{1,n} - T_b (n=1,2,3,\ldots k) \quad (2)$$

The second information TI2 includes relative time information expressed by Equation 3 below.

$$T'_{2,n} = T_{2,n} - T_b (n=1,2,3,\ldots k) \quad (3)$$

That is, the first information TI1 transmitted from the first sensor 200 and the second information TI2 transmitted from the second sensor 300 are time information synchronized with the relative time information. Thus, the first information TI1 and the second information TI2 are relative time information.

The controller 130 calculates a time difference, for example, $\Delta T_n$, between the first detection time $T_{1,1}$ through $T_{1,k}$ and the second detection time $T_{2,1}$ through $T_{2,k}$ based on the first information TI1, the second information TI2, and the receipt time $T_b$ at which the beacon signal is received.

For example, the controller 130 calculates the time difference $\Delta T_n$ between the first detection time $T_{1,1}$ through $T_{1,k}$ and the second detection time $T_{2,1}$ through $T_{2,k}$ according to Equation 4 below.

$$\Delta T_n = T'_{2,n} - T'_{1,n} (n=1,2,3, \ldots k) \quad (4)$$

Figure 8A:
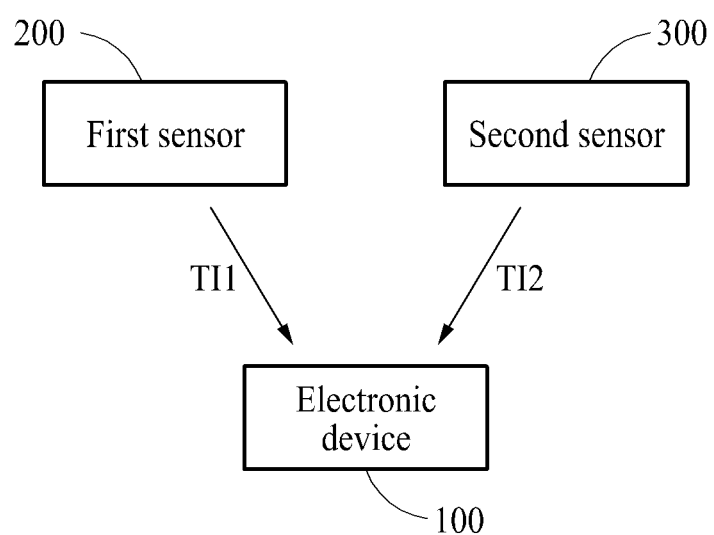
FIGS. 8A and 8B are diagrams illustrating another example of a method of measuring a time difference between detection times.
Figure 8B:
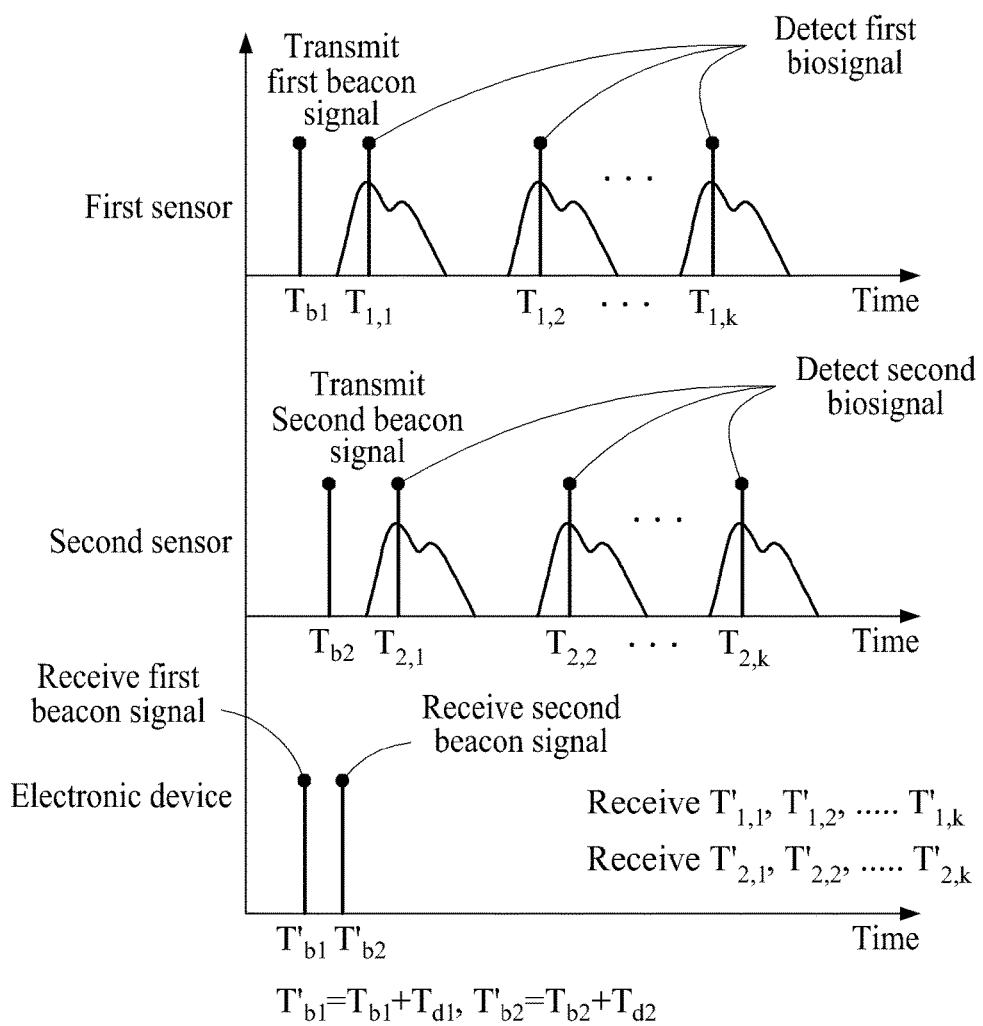

FIGS. 8A and 8B are diagrams illustrating another example of a method of measuring a time difference between detection times.

Referring to FIGS. 8A and 8B, the first sensor 200 and the second sensor 300 generate respective beacon signals and transmit the beacon signals to the electronic device 100. For example, the first sensor 200 generates a first beacon signal and transmits the generated first beacon signal to the electronic device 100. Similarly, the second sensor 300 generates a second beacon signal and transmits the generated second beacon signal to the electronic device 100.

The first sensor 200 is synchronized based on the first beacon signal, and the second sensor 300 is synchronized based on the second beacon signal. For example, the first sensor 200 is synchronized based on a transmission time $T_{b1}$ at which the first beacon signal is transmitted, and the second sensor 300 is synchronized based on a transmission time $T_{b2}$ at which the second beacon signal is transmitted.

A first detection time, for example, $T_{1,1}$, $T_{1,2}$, and $T_{1,k}$, at which a first biosignal is detected by the first sensor 200 is synchronized based on the transmission time $T_{b1}$ at which the first beacon signal is transmitted. The first sensor 200 generates first information TI1 associated with the first detection time $T_{1,1}$ through $T_{1,k}$ at which the first biosignal is detected. The first sensor 200 generates the first information TI1 synchronized based on the transmission time $T_{b1}$ at which the first beacon signal is transmitted.

A second detection time, for example, $T_{2,1}$, $T_{2,2}$, and $T_{2,k}$, at which a second biosignal is detected by the second sensor 300 is synchronized based on a transmission time $T_{b2}$ at which the second beacon signal is transmitted. The second sensor 300 generates second information TI2 associated with the second detection time $T_{2,1}$ through $T_{2,k}$ at which the second biosignal is detected. The second sensor 300 generates the second information TI2 synchronized based on the transmission time $T_{b2}$ at which the beacon signal is transmitted.

The first information TI1 includes relative time information expressed by Equation 5 below.

$$T'_{1,n} = T_{1,n} - T_{b1} (n=1,2,3, \ldots k) \quad (5)$$

The second information TI2 includes relative time information expressed bye Equation 6 below.

$$T'_{2,n} = T_{2,n} - T_{b2} (n=1,2,3, \ldots k) \quad (6)$$

That is, the first information TI1 transmitted from the first sensor 200 and the second information TI2 transmitted from the second sensor 300 are time information synchronized with the relative time information. Thus, the first information TI1 and the second information TI2 are relative time information.

The controller 130 calculates a time difference, for example, $\Delta T_n$, between the first detection time $T_{1,1}$ through $T_{1,k}$ and the second detection time $T_{2,1}$ through $T_{2,k}$ based on the first information TI1, the second information TI2, a receipt time $T'_{b1}$ at which the first beacon signal is received, and a receipt time $T'_{b2}$ at which the second beacon signal is received.

For example, the controller 130 calculates the time difference $\Delta T_n$ between the first detection time $T_{1,1}$ through $T_{1,k}$ and the second detection time $T_{2,1}$ through $T_{2,k}$ according to Equation 7 below.

$$\Delta T_n = (T'_{2,n} + T'_{b2} - T_{d2}) - (T'_{1,n} + T'_{b1} - T_{d1})(n=1,2,3, \ldots k) \quad (7)$$

In Equation 7, "$T_{d1}$" denotes a delay time between the transmission time $T_{b1}$ at which the first beacon signal is transmitted and the receipt time $T'_{b1}$ at which the first beacon signal is received. "$T_{d2}$" denotes a delay time between the transmission time $T_{b2}$ at which the second beacon signal is transmitted and the receipt time $T'_{b2}$ at which the second beacon signal is received. In this example, the delay times $T_{d1}$ and $T_{d2}$ are considered. The delay times $T_{d1}$ and $T_{d2}$ may be calculated by simulations or experiments, and preset in the controller 130.

Figure 9A:
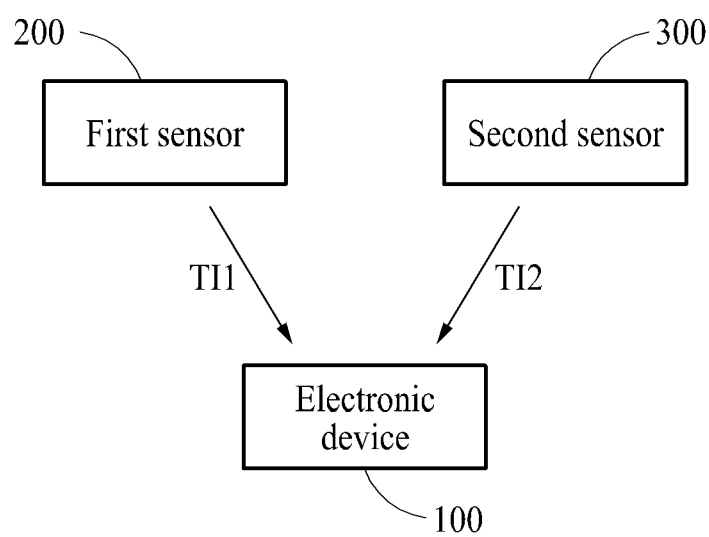

FIGS. 9A and 9B are diagrams illustrating another example of a method of measuring a time difference between detection times.

Referring to FIGS. 9A and 9B, the first sensor 200 transmits, to the electronic device 100, first information TI1 at a first detection time, for example, $T_{1,1}$, $T_{1,2}$, $\ldots T_{1,k}$, at which a first biosignal is detected. For example, the first information TI1 is information associated with the first detection time $T_{1,1}$ through $T_{1,k}$ at which the first biosignal is detected, and includes information about a waveform of the first biosignal, a peak value, a peak position, and a voltage at the first detection time $T_{1,1}$ through $T_{1,k}$.

The second sensor 300 transmits, to the electronic device 100, second information TI2 at a second detection time, for example, $T_{2,1}$, $T_{2,2}$, $\ldots T_{2,k}$, at which a second biosignal is detected. For example, the second information TI2 is information associated with the second detection time $T_{2,1}$ through $T_{2,k}$ at which the second biosignal is detected, and includes information about a waveform of the second biosignal, a peak value, a peak position, and a voltage at the first detection time $T_{2,1}$ through $T_{2,k}$.

The controller 130 measures a receipt time of the first information TI1, for example, $T'_{1,1}$, $T'_{1,2}$, $\ldots T'_{1,k}$, at which the first information TI1 is received, and measures a receipt time of the second information TI2, for example, $T'_{2,1}$, $T'_{2,2}$, $\ldots T'_{2,k}$, at which the second information TI2 is received. The controller 130 calculates a time difference, for example, $\Delta T_n$, between the first detection time $T_{1,1}$ through $T_{1,k}$ and the second detection time $T_{2,1}$ through $T_{2,k}$ based on the receipt time of the first information TI1 $T'_{1,1}$ through $T'_{1,k}$ and the receipt time of the second information TI2 $T'_{2,1}$ through $T'_{2,k}$.

For example, the controller 130 calculates the time difference $\Delta T_n$ between the first detection time $T_{1,1}$ through $T_{1,k}$ and the second detection time $T_{2,1}$ through $T_{2,k}$ according to Equation 8 below.

$$\Delta T_n = (T'_{2,n} - T_{d2}) - (T'_{1,n} - T_{d1})(n=1,2,3, \ldots k) \quad (8)$$

In Equation 8, "$T_{d1}$" denotes a delay time between the first detection time $T_{1,1}$ through $T_{1,k}$ at which the first biosignal is detected and the receipt time of the first information TI1 $T'_{1,1}$ through $T'_{1,k}$. "$T_{d2}$" denotes a delay time between the second detection time $T_{2,1}$ through $T_{2,k}$ at which the second biosignal is detected and the receipt time of the second information TI2 $T'_{2,1}$ through $T'_{2,k}$. The delay times $T_{d1}$ and $T_{d2}$ may be calculated by simulations or experiments, and preset in the controller 130.

For example, as illustrated in FIGS. 2 through 4, when either one or both of the first sensor 200 and the second sensor 300 is included in the electronic device 100, a receipt time of information transmitted from the either one or both sensor to the electronic device 100 is substantially identical to a detection time at which a biosignal is detected by the either one or both sensor. That is, a delay of information to be transmitted from the either one or both sensor to the electronic device 100 is insignificant when the either one or both sensor is included in the electronic device 100.

Figure 10:
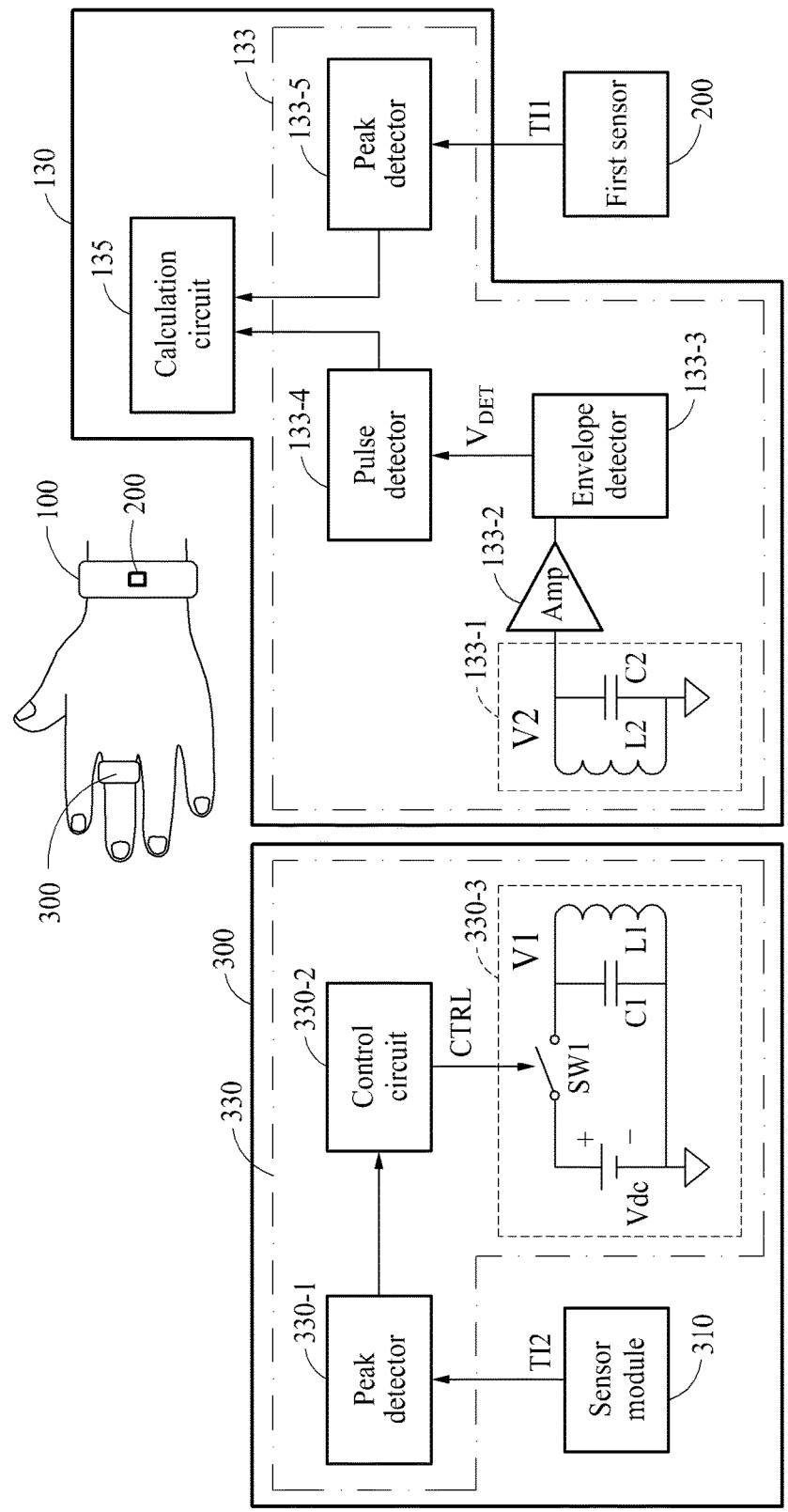
FIG. 10 is a diagram illustrating an example of a controller to perform the method of measuring a time difference between detection times illustrated in FIGS. 9A and 9B.
Figure 11:
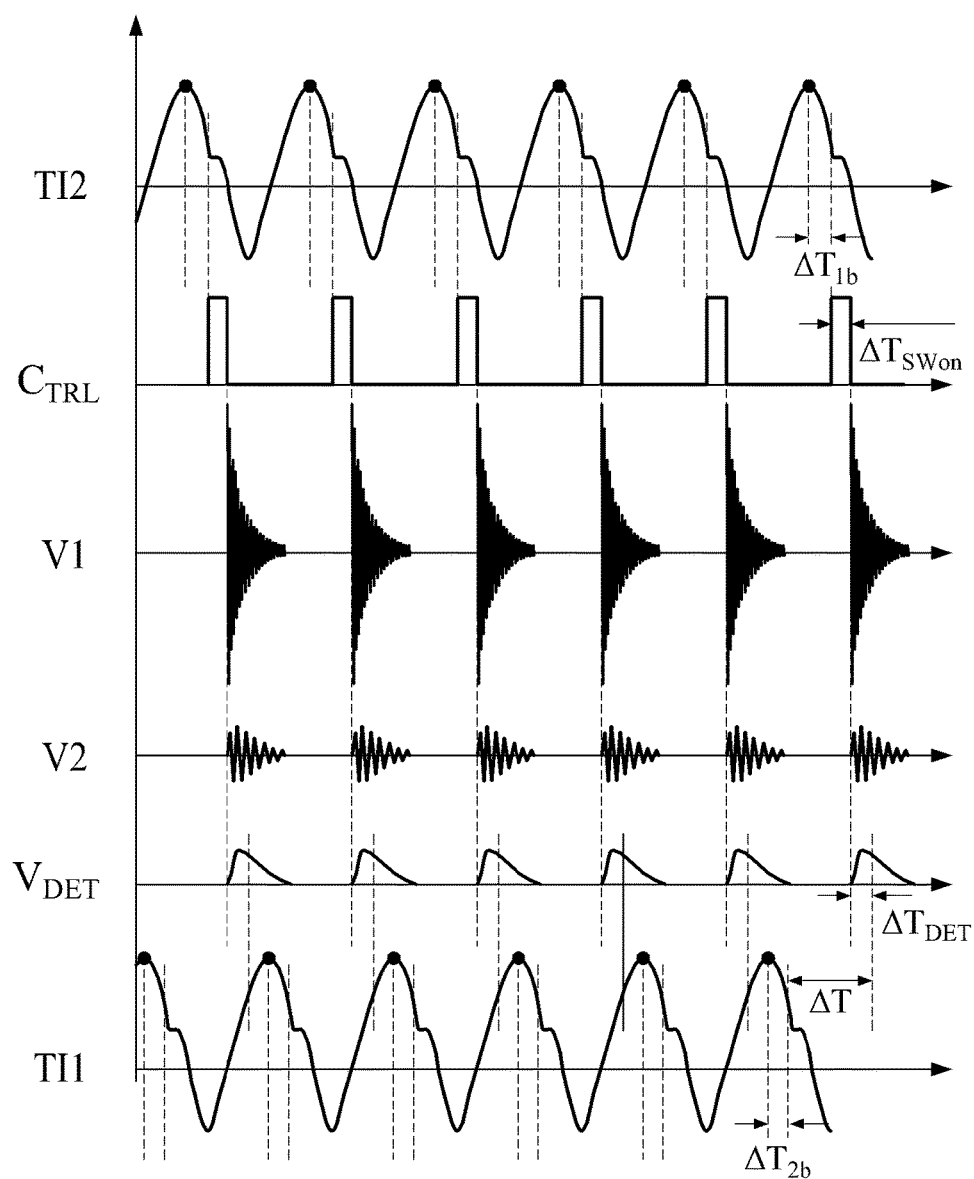
FIG. 11 is a graph illustrating an example of a measuring method performed by the controller illustrated in FIG. 10.

FIG. 10 is a diagram illustrating an example of the controller 130 to perform the method of measuring a time difference between detection times illustrated in FIGS. 9A and 9B. FIG. 11 is a graph illustrating an example of a measuring method performed by the controller 130 illustrated in FIG. 10.

In FIG. 10, the interface 110 is omitted for ease of description. Referring to the example of FIG. 10, the first sensor 200 is included in the electronic device 100, and the first sensor 200 and the electronic device 100 are connected by a wire. The second sensor 300 is provided as a ring-type device, and the electronic device 100 is provided as a watch-type wearable device. However, the second sensor 300 and the electronic device 100 are not limited to these examples, and thus the second sensor 300 and the electronic device 100 may be worn on any portion of a body.

Referring to FIGS. 10 and 11, the first sensor 200 transmits first information TI1 to the controller 130 at a first detection time at which a first biosignal is detected, and the second sensor 300 transmits second information 112 to the controller 130 at a second detection time at which a second biosignal is detected.

The second sensor 300 includes a sensor module 310 and a communication circuit 330.

The sensor module 310 generates the second information TI2 at the second detection time at which the second biosignal is detected.

The communication circuit 330 transmits the second information TI2 to the controller 130. The communication circuit 330 includes a peak detector 330-1, a control circuit 330-2, and a resonator 330-3.

The peak detector 330-1 detects a peak of the second biosignal from the second information TI2.

The control circuit 330-2 generates a control CTRL to control an ON and OFF operation of a switch SW1 included in the resonator 330-3 in response to a result of the detecting by the peak detector 330-1.

The switch performs the ON and OFF operation in response to the control signal. For example, the switch is turned on in response to an activated control signal, and turned off in response to an inactivated control signal. In addition, the switch controls a supply of power Vdc to the resonator 330-3 in response to the control signal. For example, when the switch is turned on in response to the activated control signal, the power Vdc is supplied to the resonator 330-3. When the switch is turned off in response to the inactivated control signal, the power Vdc is not supplied to the resonator 330-3.

The resonator 330-3 generates a first resonance signal V1 by charging and discharging. For example, when the switch is turned on in response to the activated control signal, the power Vdc is supplied to the resonator 330-3, and the resonator 330-3 is thus charged. When the switch is turned off in response to the inactivated control signal, the power Vdc is not supplied to the resonator 330-3, and the resonator 330-3 is thus discharged. That is, as the resonator 330-3 is discharged, the first resonance signal V1 is generated.

Although the communication circuit 330 is included in the second sensor 300 in FIG. 10, the communication circuit 330 may be disposed outside the second sensor 300 and provided as a ring-type device together with the second sensor 300.

The controller 130 includes a measurement circuit 133 and a calculation circuit 135.

The measurement circuit 133 measures a receipt time of the first information TI1 at which the first information TI1 is received, and measures a receipt time of the second information TI2 at which the second information TI2 is received. The measurement circuit 133 includes a resonator 133-1, an amplifier 133-2, an envelope detector 133-3, a pulse detector 133-4, and a peak detector 133-5. The measurement circuit 133 may correspond to the interface 110 of FIG. 5. For example, as illustrated in FIG. 5, the measurement circuit 133 may be disposed outside the controller 130 and may perform substantially identical operations as the interface 110.

The resonator 133-1 generates a second resonance signal V2 by resonance along with the resonator 330-3 of the second sensor 300. The second resonance signal V2 is induced by mutual resonance between the resonator 133-1 and the resonator 330-3.

The amplifier 133-2 amplifies an amplitude, or a magnitude, of the second resonance signal V2. The envelope detector 133-3 detects an envelope $V_{DET}$ of the amplified second resonance signal. The pulse detector 133-4 measures the receipt time of the second information TI2 by detecting energy from the detected envelope.

The peak detector 133-5 measures the receipt time of the first information TI1 by detecting a peak of the first biosignal from the first information TI1. The first sensor 200 may be included in the electronic device 100, and the receipt time of the first information TI1 may be the detection time at which the first biosignal is detected.

The calculation circuit 135 calculates a time difference PTT between the first detection time and the second detection time based on the receipt time of the first information TI1 and the receipt time of the second information TI2.

The calculation circuit 135 calculates the time difference PTT between the first detection time and the second detection time according to Equation 9 below.

$$PTT = \Delta T + \Delta T_{2b} - \Delta T_{1b} - \Delta T_{SWon} - \Delta T_{DET} \quad (9)$$

In Equation 9, and as illustrated in FIG. 11, "$\Delta T$" denotes a difference between the receipt time of the first information TI1, which is the first detection time of the first biosignal, and the receipt time of the second information TI2. "$\Delta T_{1b}$" and "$\Delta T_{2b}$" denote delay times needed for peak detection, "$\Delta T_{SWon}$" denotes a period of time during which the switch is in the ON state, and "$\Delta T_{DET}$" denotes a delay time needed for pulse detection.

Figure 12:
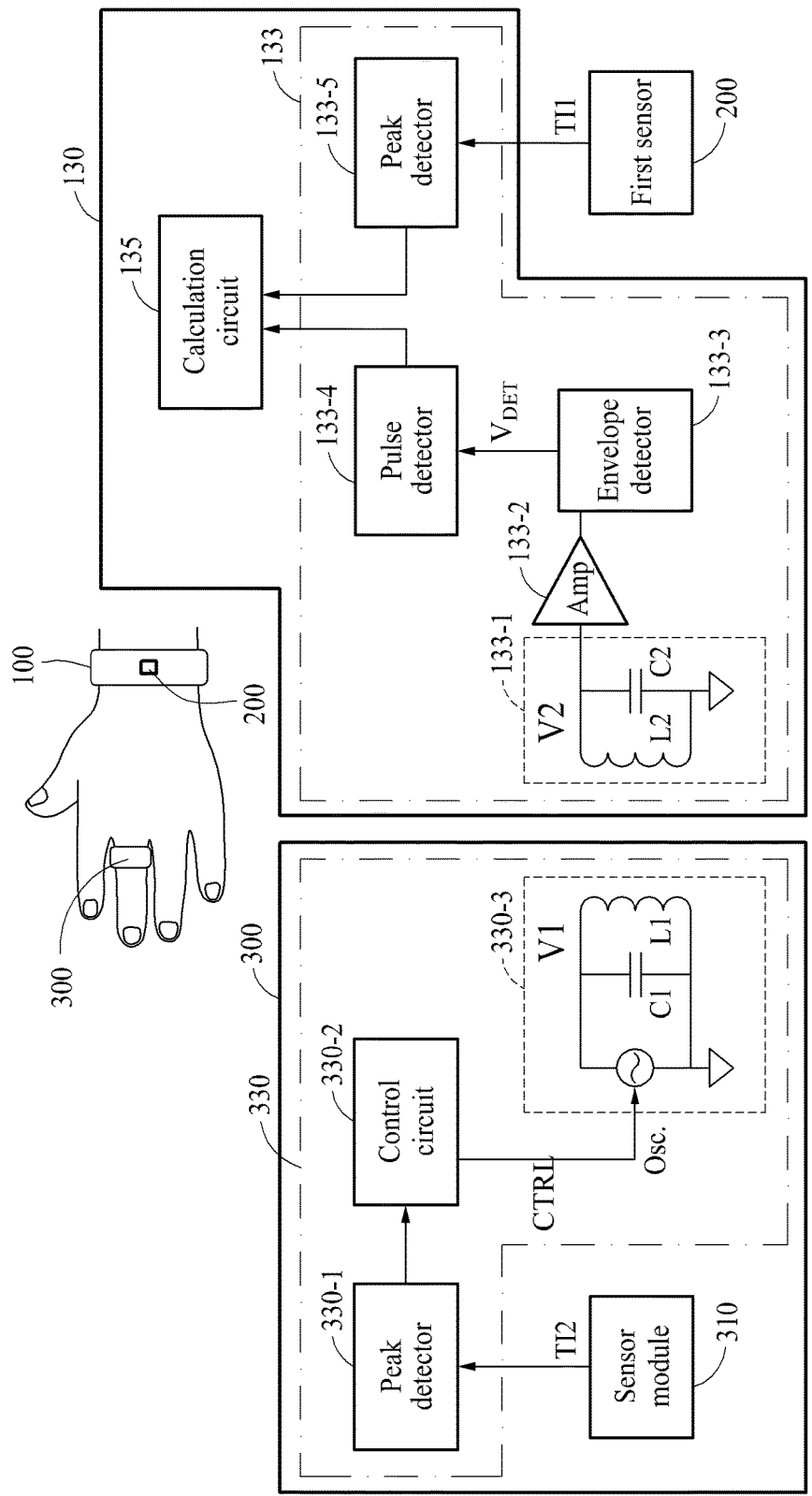
FIG. 12 is a diagram illustrating another example of a controller to perform the method of measuring a time difference between detection times illustrated in FIGS. 9A and 9B.
Figure 13:
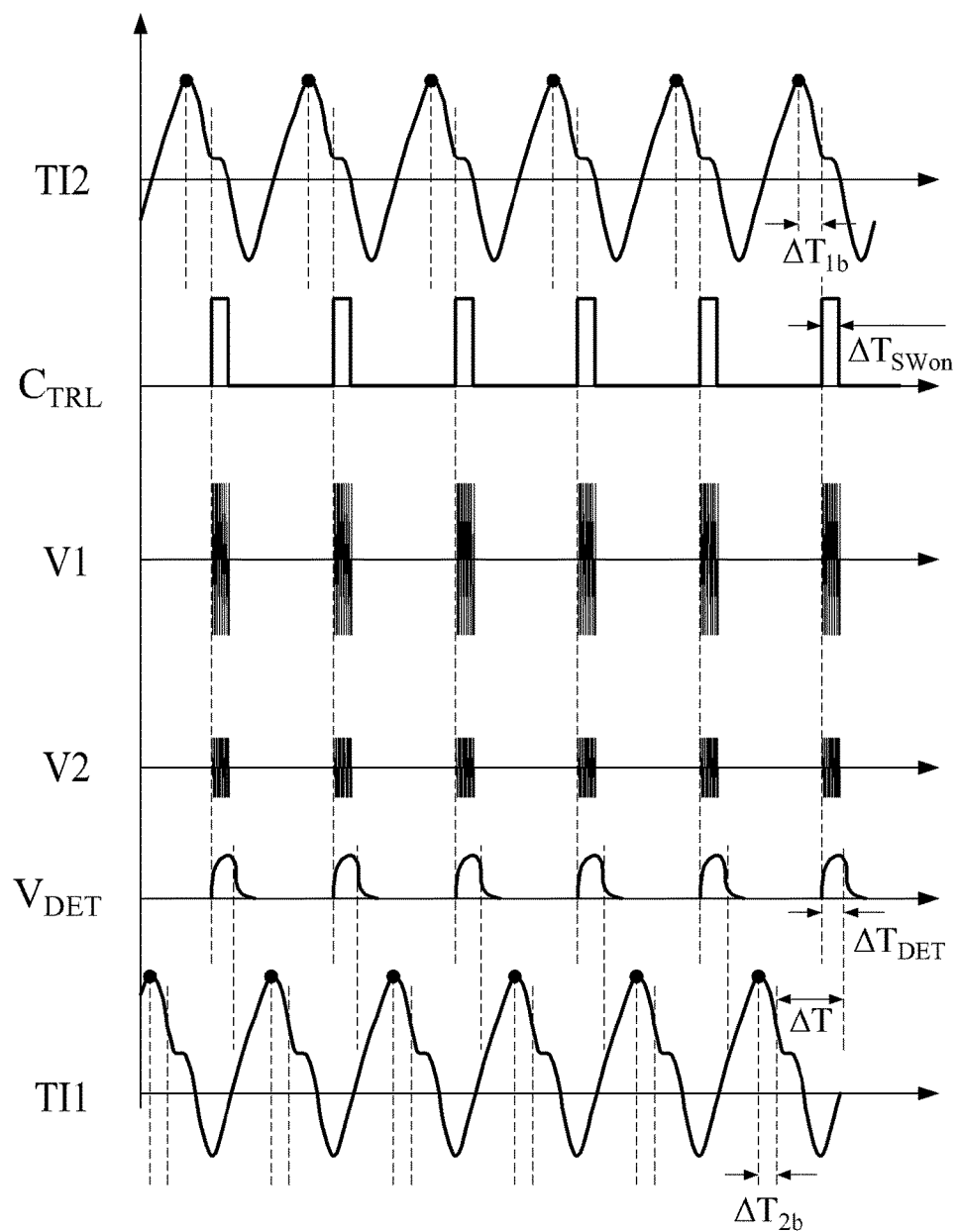
FIG. 13 is a graph illustrating an example of a measuring method performed by the controller illustrated in FIG. 12.

FIG. 12 is a diagram illustrating another example of the controller 130 to perform the method of measuring a time difference between detection times illustrated in FIGS. 9A and 9B. FIG. 13 is a graph illustrating an example of a measuring method performed by the controller 130 illustrated in FIG. 12.

Referring to FIGS. 12 and 13, components and operations of the controller 130 of FIG. 12 are substantially the same as the components and operations of the controller 130 of FIG. 10, except a first resonator 133-3 of a measurement circuit 133 of FIG. 12.

The switch SW1 and the power Vdc of the resonator 330-3 of the second sensor 300 in FIG. 10 are replaced by an oscillator Osc of a resonator 330-3 in FIG. 12.

The oscillator operates in response to a commencement of an activated control signal CTRL, and the resonator 330-3 generates a first resonance signal V1. Thus, $\Delta T_{SW_{on}}$ in Equation 9, which denotes the period of time during which the switch SW1 in FIG. 10 is in the ON state, need be considered.

A calculation circuit 135 calculates a time difference PTT between the first detection time and the second detection time according to Equation 10 below obtained by modifying Equation 9.

$$PTT=\Delta T+\Delta T_{2b}-\Delta T_{1b}-\Delta T_{DET} \qquad (10)$$

With reference to FIGS. 10 through 13, a circular coil is embedded in the second sensor 300 along a circumference of a finger of a user, and a circular coil is embedded in the electronic device 100 along a circumference of a wrist of the user. In addition, the circuits 330 and 133 are coupled by a magnetic field, and thus the second sensor 300 and the electronic device 100 may communicate through a magnetic communication method.

The controller 130 receives the second information TI2 from the second sensor 300 through the coils coupled by the magnetic field. As illustrated in FIG. 10, the controller 130 receives the second information TI2 through mutual magnetic induction between the coils occurring due to the charging and discharging of the resonator 330-3. As illustrated in FIG. 12, the controller 130 receives the second information TI2 through mutual magnetic induction between the coils occurring due to the oscillator Osc switching between the ON and OFF states.

In addition, power may be wirelessly supplied to the second sensor 300 and the electronic device 100. For example, the controller 130 may transmit power to the second sensor 300 through the coils coupled by the magnetic field.

Although the second sensor 300 is provided as a ring-type device and disposed outside the electronic device 100, the second sensor 300 is not limited thereto. The controller 130 may communicate with one or both of the first sensor 200 and the second sensor 300 through the coils coupled through the magnetic field using the magnetic communication method.

The magnetic communication method may be more advantageous compared to other communication technology such as Bluetooth due to a smaller amount of damage to a human body, and information leakage may be prevented due to a lower possibility of radiation.

Figure 14:
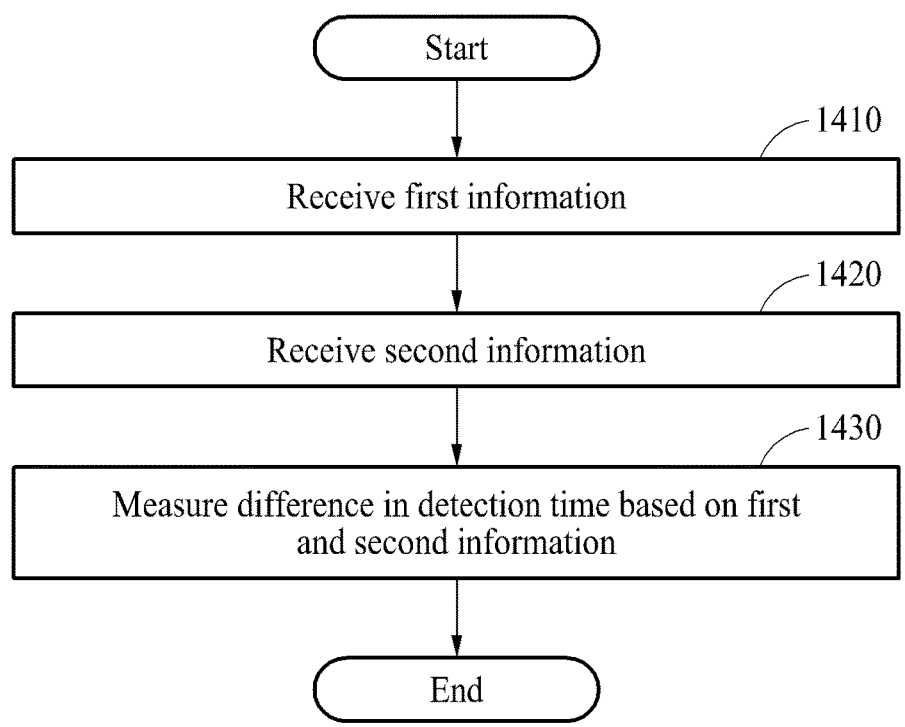
FIG. 14 is a flowchart illustrating an example of an operating method of the electronic device illustrated in FIG. 5.

FIG. 14 is a flowchart illustrating an example of an operating method of the electronic device 100 illustrated in FIG. 5.

Referring to FIG. 14, in operation 1410, the interface 110 receives, from the first sensor 200, first information associated with a first detection time of a first biosignal at which the first biosignal is detected.

In operation 1420, the interface 110 receives, from the second sensor 300, second information associated with a second detection time of a second biosignal at which the second biosignal is detected.

In operation 1430, the controller 130 measures a time difference between the first detection time and the second detection time based on the first information and the second information.

The electronic device 100, the interface 110, the controller 130, the measurement circuit 133, the resonator 133-1, the amplifier 133-2, the envelope detector 133-3, the pulse detector 133-4, the peak detector 133-5, the calculation circuit 135, the first sensor 200, the second sensor 300, the sensor module 310, the communication circuit 330, the peak detector 330-1, the control circuit 330-2, the resonator 330-3, the time device 400, and the beacon device 500 illustrated in FIGS. 1-5, 6A, 7A, 8A, 9A, 10, and 12 that perform the operations described herein with respect to FIG. 1-14 are implemented by hardware components. Examples of hardware components include controllers, sensors, generators, drivers, memories, comparators, arithmetic logic units, adders, subtractors, multipliers, dividers, integrators, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-14. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The method illustrated in FIG. 14 that performs the operations described herein with respect to FIGS. 1-14 is performed by computing hardware, for example, one or more processors or computers, as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of measuring a time difference between detection times, the method comprising:
   receiving, at a controller, from a first sensor, first information associated with a first detection time at which a peak value of a first biosignal is detected;
   receiving, at the controller, from a second sensor, second information of a peak value of a second biosignal associated with a second detection time using a resonance signal generated through mutual magnetic induction between a coil disposed at the controller and a coil disposed at the second sensor; and
   measuring a time difference between the first detection time and the second detection time based on the first information and the second information.

2. The method of claim 1, wherein the first information and the second information are time information synchronized with relative time information.

3. The method of claim 1, further comprising receiving a beacon signal;
   wherein the measuring comprises calculating the time difference between the first detection time and the second detection time based on the first information, the second information, and a receipt time at which the beacon signal is received.

4. The method of claim 3, wherein the first information and the second information are time information synchronized based on the receipt time at which the beacon signal is received.

5. The method of claim 1, further comprising:
   receiving a first beacon signal transmitted from the first sensor; and
   receiving a second beacon signal transmitted from the second sensor;
   wherein the measuring comprises calculating the time difference between the first detection time and the second detection time based on the first information, the second information, a receipt time at which the first beacon signal is received, and a receipt time at which the second beacon signal is received.

6. The method of claim 5, wherein the first information is time information synchronized based on the first beacon signal; and
   the second information is time information synchronized based on the second beacon signal.

7. The method of claim 1, wherein the measuring comprises:
   measuring a first receipt time at which the first information is received;
   measuring a second receipt time at which the second information is received; and
   calculating the time difference between the first detection time and the second detection time based on the first receipt time and the second receipt time.

8. The method of claim 1, further comprising calculating a time difference $\Delta T_n$ between the first detection time and the second detection time according to $\Delta T_n = (T'_{2,n} - T_{d2}) - (T'_{1,n} - T_{d1})$, n=1, 2, 3, ... k, wherein $T_{d1}$ is a delay time between the first detection time $T_{1,1}$ through $T_{1,k}$ at which the first biosignal is detected and a receipt time of the first information $T'_{1,1}$ through $T'_{1,k}$, and $T_{d2}$ is a delay time between the second detection time $T_{2,1}$ through $T_{2,k}$ at which the second biosignal is detected and the receipt time of the second information $T'_{2,1}$ through $T'_{2,k}$.

9. The method of claim 8, wherein the delay time $T_{d1}$ is equal to a time from the peak value to a subsequent peak value.

10. An electronic device comprising:
    a controller; and
    an interface configured to receive, from a first sensor, first information associated with a first detection time at which a peak value of a first biosignal is received, and receive, from a second sensor, second information of a peak value of a second biosignal associated with a second detection time, using a resonance signal generated through mutual magnetic induction between a coil disposed at the controller and a coil disposed at the second sensor, and
    wherein the controller is configured to measure a time difference between the first detection time and the second detection time based on the first information and the second information.

11. The electronic device of claim 10, wherein the first information and the second information are time information synchronized with relative time information.

12. The electronic device of claim 10, wherein the interface is further configured to receive, from a beacon device, a beacon signal; and
  the controller is further configured to calculate the time difference between the first detection time and the second detection time based on the first information, the second information, and a receipt time at which the beacon signal is received.

13. The electronic device of claim 12, wherein the first information and the second information are time information synchronized based on the receipt time at which the beacon signal is received.

14. The electronic device of claim 10, wherein the interface is further configured to receive a first beacon signal transmitted from the first sensor, and receive a second beacon signal transmitted from the second sensor; and
  the controller is further configured to calculate the time difference between the first detection time and the second detection time based on the first information, the second information, a receipt time at which the first beacon signal is received, and a receipt time at which the second beacon signal is received.

15. The electronic device of claim 14, wherein the first information is time information synchronized based on the first beacon signal; and
  the second information is time information synchronized based on the second beacon signal.

16. The electronic device of claim 10, wherein the controller is further configured to measure a first receipt time at which the first information is received and a second receipt time at which the second information is received, and calculate the time difference between the first detection time and the second detection time based on the first receipt time and the second receipt time.

17. The electronic device of claim 16, wherein the controller is further configured to receive either one or both of the first information and the second information using the coils.

18. The electronic device of claim 17, wherein the controller is further configured to receive the either one or both of the first information and the second information by the mutual magnetic induction between the coils occurring due to charging and discharging of a resonator.

19. The electronic device of claim 17, wherein the controller is further configured to receive the either one or both of the first information and the second information by the mutual magnetic induction between the coils occurring due to an oscillator switching between ON and OFF states.

20. The electronic device of claim 17, wherein the controller is further configured to transmit power to either one or both of the first sensor and the second sensor using the coils coupled by the magnetic field.

* * * * *